(12) United States Patent
Rieping et al.

(10) Patent No.: US 8,143,032 B1
(45) Date of Patent: Mar. 27, 2012

(54) ALLELES OF THE THRA GENE OF ENTEROBACTERIACEAE

(75) Inventors: Mechthild Rieping, Bielefeld (DE); Georg Thierbach, Bielefeld (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 13/082,542

(22) Filed: Apr. 8, 2011

Related U.S. Application Data

(63) Continuation of application No. 12/418,827, filed on Apr. 6, 2009, now abandoned, which is a continuation of application No. 11/451,492, filed on Jun. 13, 2006, now abandoned, which is a continuation of application No. 10/412,334, filed on Apr. 14, 2003, now abandoned, which is a continuation of application No. 10/282,186, filed on Oct. 29, 2002, now abandoned.

(60) Provisional application No. 60/330,711, filed on Oct. 29, 2001.

(51) Int. Cl.
| | |
|---|---|
| *C12P 13/04* | (2006.01) |
| *C12P 13/08* | (2006.01) |
| *C12N 9/00* | (2006.01) |
| *C12N 9/02* | (2006.01) |
| *C12N 1/20* | (2006.01) |
| *C12N 15/00* | (2006.01) |
| *C07H 21/04* | (2006.01) |

(52) U.S. Cl. ........ 435/115; 435/106; 435/183; 435/189; 435/252.3; 536/23.6

(58) Field of Classification Search ........................ None
See application file for complete search history.

(56) References Cited

OTHER PUBLICATIONS

Houchins, J. et al. (1993) "Genomic Structure of NKG5, a Human NK and T Cell-Specific Activation Gene" Immunogenetics 37(2):102-107.
Reiger, R. et al. (1991) "Glossary of Genetics, Classical and Molecular" 5th Edition, 16-17.
Rees, W. (1995) "The Biosynthesis of Threonine by Mammalian Cells: Expression of a Complete Bacterial Biosynthetic Pathway in an Animal Cell" Biochem J. 309:999-1007.
Chica, R. et al. (2005) "Semi-Rational Approaches to Engineering Enzyme Activity: Combining the Benefits of Directed Evolution and Rational Design" Current Opinion in Biotechnology 16:378-384.
Sen, S. et al. (2007) "Developments in Directed Evolution for Improving Enzyme Functions" Appl. Biochem. Biotechnol. 143(3):212-223.

*Primary Examiner* — Christian Fronda
(74) *Attorney, Agent, or Firm* — Smith, Gambrell & Russell, LLP

(57) ABSTRACT

Alleles of the thrA gene from Enterobacteriaceae encoding desensitized aspartokinase I-homoserine dehydrogenase I enzymes and methods for the fermentative production of L-threonine using bacteria containing these alleles.

18 Claims, No Drawings

US 8,143,032 B1

ALLELES OF THE THRA GENE OF ENTEROBACTERIACEAE

CROSS REFERENCE TO RELATED APPLICATIONS

This application is a continuation of U.S. patent application Ser. No. 12/418,827, filed 6 Apr. 2009 now abandoned, pending, which is a continuation of U.S. patent application Ser. No. 11/451,492, filed 13 Jun. 2006, allowed abandoned, which is a continuation of U.S. patent application Ser. No. 10/412,334, filed 14 Apr. 2003, abandoned, which is a continuation of U.S. patent application Ser. No. 10/282,186, filed 29 Oct. 2002, abandoned, which claims the benefit of U.S. Provisional Application Ser. No. 60/330,711, filed 29 Oct. 2001.

BACKGROUND OF THE INVENTION

1. Field of the Invention

The invention relates to alleles of the thrA gene of Enterobacteriaceae coding for desensitized aspartokinase I-homoserine dehydrogenase I enzymes and methods for the fermentative production of L-threonine using bacteria of the family Enterobacteriaceae containing these alleles.

2. Background Information

L-threonine is used in human medicine, in the pharmaceutical industry, in the food industry and particularly in animal nutrition.

It is known that L-threonine is produced by fermenting strains of Enterobacteriaceae, especially *Escherichia coli* (*E. coli*) and *Serratia marcescens*. Because of its great importance, constant work is being carried out to improve production methods. Method improvements can relate to fermentation measures such as, for example, agitation and supplying with oxygen or the composition of the nutrient media such as, for example, the concentration of sugar during the fermentation or can concern the workup to product form by, for example, ion exchange chromatography or concern the intrinsic performance properties of the microorganism itself.

Methods of mutagenesis, selection and mutant selection are used to improve the performance properties of these microorganisms. In this manner, strains are obtained that are resistant to antimetabolites such as, for example, the threonine analogue α-amino-β-hydroxyvaleric acid (AHV) or are auxotrophic for metabolites important in regulation and that produce L-threonine.

For several years methods of recombinant DNA technology for the improvement of strains of the family Enterobacteriaceae producing amino acids have also been used to amplify individual amino-acid biosynthesis genes and examine the effect on production.

Two important reaction steps in the biosynthesis of L-threonine are the aspartokinase reaction and the homoserine dehydrogenase reaction. Aspartokinase catalyzes the conversion of L-asparaginic acid to aspartyl phosphoric acid. Homoserine dehydrogenase catalyzes the conversion of asparaginic acid semialdehyde to homoserine.

There are three isoenymes in *Escherichia coli* K-12 and *Serratia marcescens* which catalyze these reactions: Aspartokinase III encoded by the lysC gene, the bifunctional enzyme aspartokinase II-homoserine dehydrogenase II encoded by the metL gene, and the bifunctional enzyme aspartokinase I-homoserine dehydrogenase I encoded by the thrA gene. The enzyme aspartokinase I-homoserine dehydrogenase I in particular is responsible for the biosynthesis of L threonine. Summarizing presentations for this are found, for example, in the textbook of Frederick C. Neidhard "*Escherichia coli* and *Salmonella*, Cellular and Molecular Biology" ($2n^d$ edition, ASM press, USA, Washington D.C., 1996).

The nucleotide sequence of the thrA gene of *Escherichia coli* is known and available under the accession number AE000111 in the National Center for Biotechnology Information (NCBI, Bethesda, Md., USA). Mutants were isolated by Saint-Girons and Margarita (Journal of Bacteriology 124, 1137-1141 (1975)) with the aid of the threonine analogue α-amino-β-hydroxyvaleric acid (AHV) which mutants were able to excrete L-threonine. The mutation site was, according to the authors, in the thrA gene, and the enzyme aspartokinase I-homoserine dehydrogenase I was resistant to inhibition by threonine.

The nucleotide sequence of the thrA gene of *Serratia marcescens* is known and available under the accession number X60821 in the NCBI. Mutants were isolated from *Serratia marcescens* Sr41 which mutants produce L-threonine and have mutations in the thrA gene. These thrA alleles were sequenced and are described in Omori et al. (Journal of Bacteriology 175, 785-794 (1993)). The proteins encoded by these thrA alleles have amino-acid exchanges at position 330 and position 352 and position 479 of the aspartokinase I-homoserine dehydrogenase I protein.

SUMMARY OF THE INVENTION

Object of the Invention

It is an object of the invention to provide novel alleles of the thrA gene and methods for the improved fermentative production of L-threonine.

DESCRIPTION OF THE INVENTION

The invention provides replicable nucleotide sequences (DNA) stemming from Enterobacteriaceae, especially *Escherichia coli*, that encodes the enzyme aspartokinase I-homoserine dehydrogenase I. The associated amino-acid sequences in SEQ ID NO:2 contain every proteinogenic amino acid at position 345 except L-serine.

The invention also provides a replicable nucleotide sequence (DNA) from Enterobacteriaceae, especially *Escherichia coli*, that encodes the enzyme aspartokinase I-homoserine dehydrogenase I. The associated amino-acid sequence contains L-phenylalanine at position 345, shown in SEQ ID NO:4.

The invention also provides a replicable nucleotide sequence (DNA) stemming from Enterobacteriaceae, especially *Escherichia coli*, that encodes the enzyme aspartokinase I-homoserine dehydrogenase I. The base sequence of said nucleotide sequence contains thymine at position 1034, shown in SEQ ID NO:3.

The invention also includes plasmids (vectors) that comprise the nucleotide sequences in accordance with the invention and replicate, if needed, in Enterobacteriaceae.

The invention also includes Enterobacteriaceae that comprise the nucleotide sequences of the invention and in which the nucleotide sequences encoding aspartokinase I-homoserine dehydrogenase I are preferably present in an overexpressed manner. Another proteinogenic amino acid is contained in the associated amino-acid sequences at position 345 of SEQ ID NO:2.

The term "overexpression" denotes an elevation of the intracellular concentration or activity of the proteins encoded by the particular gene or allele, in the present instance the aspartokinase I-homoserine dehydrogenase I enzymes of the invention.

The activity or concentration of the corresponding protein is elevated in general by at least 10%, 25%, 50%, 75%, 100%, 150%, 200%, 300%, 400% or 500% up to a maximum of 1000% or 2000% relative to the activity or concentration of the protein in the original microorganism by the measures of overexpression.

The invention also provides a method of producing L-threonine or fodder additives containing L-threonine in which the following steps are carried out:
a) Fermentation of Enterobacteriaceae containing nucleotide sequences encoding the enzyme aspartokinase I-homoserine dehydrogenase I; the L-serine is replaced in the associated amino-acid sequences at position 345 by another proteinogenic amino acid, preferably L-phenylalanine,
b) Enrichment of the L-threonine in the fermentation broth,
c) Isolation of the L-threonine or fodder additive containing L-threonine from the fermentation broth,
d) optionally with components from the fermentation broth and/or the biomass ($\geq$0 to 100%).

The term "proteinogenic amino acids" denotes all amino acids that are components of proteins or polypeptides. They are in particular: L-asparaginic acid, L-asparagine, L-threonine, L-serine, L-glutamic acid, L-glutamine, glycine, L-alanine, L-cysteine, L-selenocysteine, L-valine, L-methionine, L-isoleucine, L-leucine, L-tyrosine, L-phenylalanine, L-histidine, L-lysine, L-tryptophane, L-proline and L-arginine.

The nucleotide sequence of the wild form of the thrA gene of *Escherichia coli* is shown in SEQ ID NO:1. It can also be obtained from the genome sequence of *Escherichia coli* published by Blattner et al. (Science 277, 1453-1462 (1997)).

Mutagenesis methods known to those of skill in the art are used to produce the thrA alleles of the invention that encode a feedback-resistant aspartokinase I-homoserine dehydrogenase I characterized by an amino-acid exchange at position 345 of SEQ ID NO:2. Classic in vivo mutagenesis methods using mutagenic substances such as, for example, N-methyl-N'-nitro-N-nitrosoguanidine or ultraviolet light can be used for the mutagenesis.

Furthermore, in vitro methods such as, for example, a treatment with hydroxylamine (J. H. Miller: A Short Course in Bacterial Genetics. A Laboratory Manual and Handbook for *Escherichia coli* and Related Bacteria, Cold Spring Harbor Laboratory Press, Cold Spring Harbor, 1992) or mutagenic oligonucleotides (T. A. Brown: Gentechnologie für Einsteiger, Spektrum Akademischer Verlag, Heidelberg, 1993) or the polymerase chain reaction (PCR) as described in the manual of Newton and Graham (PCR, Spektrum Akademischer Verlag, Heidelberg, 1994) can be used for the mutagenesis.

Further instructions for producing mutations are known in the art and can be found in textbooks on genetics and molecular biology such as, for example, the textbook by Knippers ("Molekulare Genetik", 6$^{th}$ edition, Georg Thieme Verlag, Stuttgart, Germany, 1995), the textbook by Winnacker ("Gene and Klone", VCH Verlagsgesellschaft, Weinheim, Germany, 1990) or the textbook by Hagemann ("Allgemeine Genetik", Gustav Fischer Verlag, Stuttgart, 1986).

When using in vivo mutagenesis methods the mutagenized population of the bacterial strain is applied onto a minimal agar containing AHV and the culture incubated at a temperature of approximately 25 to 40° C. Those mutants that produce L-threonine are subsequently selected from the AHV-resistant mutants. The thrA alleles contained in the mutants can then be isolated, examined and sequenced. Instructions for sequencing are to be found, for example, in Sanger et al. (Proceedings of the National Academy of Sciences of the United States of America, 74:5463-5467, (1977)).

When using in vitro methods, the thrA gene as known in the art is amplified starting from isolated total DNA of a wild type strain with the aid of a polymerase chain reaction (PCR), optionally cloned into suitable plasmid vectors and the DNA subsequently subjected to the mutagenesis method. An expert in the art will find instructions for the amplification of DNA sequences with the aid of a polymerase chain reaction in, among other places, the manual by Gait: Oligonucleotide Synthesis: A Practical Approach (IRL Press, Oxford, UK, 1984) and in Newton and Graham: PCR (Spectrum Akademischer Verlag, Heidelberg, Germany, 1994). Suitable thrA alleles are subsequently selected and examined with the methods described above.

The work on the present invention was successful in isolating the thrA allele that encodes a feedback-resistant aspartokinase I-homoserine dehydrogenase I and is shown in SEQ ID NO:3. The gene product or protein formed is shown in SEQ ID NO:4.

It is known that enzymes proper to the host, so-called amino peptidases, can split off the N-terminal amino acid L-methionine and formyl methionine of the protein formed.

The thrA alleles of the invention can be inserted into suitable strains by the method of gene or allele exchange.

A customary method is the method of gene exchange with the aid of a conditionally replicating pSC101 derivative pMAK705 described by Hamilton et al. (Journal of Bacteriology 174, 4617-4622 (1989)). Other methods known in the art such as, for example, the method of Martinez-Morales et al. (Journal of Bacteriology 1999, 7143-7148 (1999)) or the method of Boyd et al. (Journal of Bacteriology 182, 842-847 (2000)) can also be used.

It is likewise possible to introduce the thrA alleles of the invention into different strains by conjugation or transduction.

It was further found in the work on the present invention that an improvement of the production of L-threonine occurs after overexpression of the thrA alleles of the invention.

In order to achieve overexpression the copy number of the alleles can be increased or the promoter- and regulation region or the ribosome bonding site located upstream from the structural gene can be mutated. Expression cassettes inserted upstream from the structural gene act in the same manner. It is additionally possible to increase the expression in the course of the fermentative production of L-threonine by inducible promoters. The expression is also improved by measures for extending the life of the m-RNA. Furthermore, the enzymatic activity is also improved by preventing the degradation of the enzymatic protein. The genes or gene constructs can either be present in plasmids with differing copy numbers or integrated and amplified in the chromosome. Alternatively, overexpression of the alleles concerned can be achieved by altering the media composition and the culture conditions.

An expert in the art will find instructions for the above in, among other places, Chang and Cohen (Journal of Bacteriology 134: 1141-1156 (1978)) and Hartley and Gregori (Gene 13: 347-353 (1981)), Amann and Brosius (Gene 40: 183-190 (1985), de Broer et al. (Proceedings of the National Academy of Sciences of the United States of America 80: 21-25 (1983)), LaVallie et al. (BIO/TECHNOLOGY 11, 187-193 (1993)), PCT/US 97/13359, Llosa et al. (Plasmid 26: 222-224 (1991)), Quandt and Klipp (Gene 80: 161-169 (1989)), Hamilton (Journal of Bacteriology 171: 4617-4622 (1989)), Jensen and Hammer (Biotechnology and Bioengineering 58, 191-195 (1998) and in known textbooks of genetics and molecular biology.

Plasmid vectors such as, for example, cloning vectors derived from pACYC184 (Bartolome et al.; Gene 102, 75-78 (1991)), and vectors such as pTrc99A (Amann et al.: Gene 69: 301-315 (1988)) or pSC101 derivatives (Vocke and Bastia, Proceedings of the National Academy of Sciences USA 80 (21): 6557-6561 (1983)) which plasmid vectors are replicable in Enterobacteriaceae can be used. A strain transformed with a plasmid vector can be used in a method in accordance with the invention. This plasmid vector carries at least one of the thrA alleles of the invention.

The microorganisms produced in accordance with the invention can be cultivated in the batch method, fed batch method or in the repeated fed batch method. A summary of known cultivation methods can be found in the textbook by Chmiel (Bioprozesstechnik 1. Einführung in die Bioverfahrenstechnik (Gustav Fischer Verlag, Stuttgart, 1991)) or in the textbook by Storhas (Bioreactoren and periphere Einrichtungen (Vieweg Verlag, Braunschweig/Wiesbaden, 1994)).

The culture medium to be used must satisfy the requirements of the particular strains in a suitable manner. Descriptions of culture media of various microorganisms are contained in the manual "Manual of Methods for General Bacteriology" of the American Society for Bacteriology (Washington D.C., USA, 1981).

Sugar and carbohydrates such as, for example, glucose, saccharose, lactose, fructose, maltose, molasses, starch and optionally cellulose, oils and fats such as, for example, soybean oil, sunflower oil, peanut oil and coconut butter, fatty acids such as, for example, palmitic acid, stearic acid and linoleic acid, alcohols such as, for example, glycerol, and ethanol and organic acids such as, for example, acetic acid can be used as carbon source.

The following can be used as nitrogen source: Organic nitrogen-containing compounds such as peptones, yeast extract, meat extract, malt extract, corn steep liquor, soybean meal and urea or inorganic compounds such as ammonium sulfate, ammonium chloride, ammonium phosphate, ammonium carbonate and ammonium nitrate. The nitrogen sources can be used individually or as mixture.

Phosphoric acid, potassium dihydrogen phosphate or dipotassium hydrogen phosphate or the corresponding sodium-containing salts can be used as phosphorus source. The culture medium must furthermore contain metal salts such as, for example, magnesium sulfate or iron sulfate, that are necessary for growth. Finally, essential growth substances such as amino acids and vitamins can be used in addition to the above-named substances. Moreover, suitable precursors can be added to the culture medium. The cited substances used can be supplied to the culture in the form of a one-time batch or fed in during the cultivation in a suitable manner.

Basic compounds such as sodium hydroxide, potassium hydroxide, ammonia or ammonia water or acidic compounds such as phosphoric acid or sulfuric acid can be added in a suitable manner in order to regulate the pH of the culture. Antifoaming agents such as, for example, fatty-acid polyglycolic esters can be added to control the development of foam. Suitable, selectively acting substances such as, for example, antibiotics can added to the medium to maintain the stability of plasmids. Oxygen or oxygen-containing gaseous mixtures such as, for example, air are charged into the culture in order to maintain aerobic conditions. The temperature of the culture is normally approximately 25° C. to 45° C. and preferably approximately 30° C. to 40° C. The culture is continued until a maximum of L-amino acids or L-threonine has formed. This target is normally achieved within 10 to 160 hours.

The analysis of L-amino acids can take place by anion exchange chromatography with subsequent ninhydrin derivatization as described in Spackman et al. (Analytical Chemistry, 30: 1190-1206 (1958)) or it can take place by reversed phase HPLC as described in Lindroth et al. (Analytical Chemistry (1979) 51L 1167-1174).

The method of the invention serves for the fermentative production of L-threonine, L-isoleucine, L-methinine, and L-homoserine, especially L-threonine.

DETAILED DESCRIPTION OF THE INVENTION

The present invention is described in detail in the following with reference made to exemplary embodiments.

Minimal (M9) and full media (LB) used for $E.$ $coli$ are described by J. H. Miller (A Short Course in Bacterial Genetics (1992), Cold Spring Harbor Laboratory Press). The isolating of plasmid DNA from $E.$ $coli$ as well as all techniques for restriction, Klenow treatment and alkaline phosphatase treatment are carried out according to Sambrook et al. (Molecular Cloning. A Laboratory Manual (1989), Cold Spring Harbor Laboratory Press). The transformation of $E.$ $coli$ is carried out, if not otherwise described, according to Chung et al. (Proceedings of the National Academy of Sciences of the United States of America 86: 2172-2175 (1989)). P1 transductions are carried out according to Lengeler et al. (Journal of Bacteriology 124: 26-38 (1975)).

Example 1

Transduction of the scr Gene Locus into the $E.$ $Coli$ K12 Strain MG1655

The scr regulon of the naturally occurring plasmid pUR400 (Schmid et al., Molecular Microbiology 2: 1-8 (1988)) imparts the ability to utilize saccharose as a carbon source. The scr regulon can be transferred into the chromosome of $Escherichia$ $coli$ K12 with the aid of plasmid pKJL710 (Ulmke et al., Journal of Bacteriology 181: 1920-1923 (1999)), that contains the scr regulon between the two inverted sequence repetitions of transposon Tn1721 (Ubben and Schmitt, Gene 41: 145-152 (1986)), and subsequent transformation, transposition, conjugation and transduction. A strain designated by LJ210 carries the scr regulon integrated in the chromosome at the position 6 minutes according to the Berlyn map. Bacteriophage P1 is multiplied in this strain and the $E.$ $coli$ K12 strain MG1655 (Guyer et al., Cold Spring Harbor Symp., Quant. Biology 45: 135-140 (1981)) infected with the isolated phage lysate. MG 1655 transducts are obtained by plating out onto saccharose-containing (2 g/l) minimal medium, which can utilize saccharose as carbon source. A selected clone is designated by MG1655scr.

Example 2

In-Vivo Mutagenesis of Strain MG1655scr and Production of L-Threonine

Starting with MG1655scr, after incubation at 37° C. on minimal agar compounded with 2 g/l saccharose and 4 g/l DL-β-hydroxynorvaline (Sigma, Deisenhofen, Germany), spontaneous mutants are isolated that are resistant to the threonine analogue α-amino-β-hydroxyvaleric acid (AHV). Selected clones are multiplied on minimal medium with the following composition: 3.5 g/l $Na_2HPO_4.2H_2O$, 1.5 g/l KH$_2$PO$_4$, 1 g/l NH$_4$Cl, 0.1 g/l MgSO$_4$.7H$_2$O, 2 g/l saccharose, 20 g/l agar. The cultures are incubated for 5 days at 37° C. The formation of L-threonine is checked in batch cultures of 10 ml obtained in 100 ml Erlenmeyer flasks. To this end, 10 ml pre-culture medium with the following composition: 2 g/l yeast extract, 10 g/l (NH$_4$)$_2$SO$_4$, 1 g/l KH$_2$PO$_4$, 0.5 g/l MgOS$_4$.7H$_2$O, 15 g/l CaCO$_3$, 20 g/l saccharose are injected and the mixture incubated for 16 hours at 37° C. and 180 rpm on an ESR incubator of the Miner AG company (Birsfelden, Switzerland). After the incubation, the optical density (OD) of the culture suspension is determined with an LP2W photometer of the Dr. Lange company (Berlin, Germany) at a measuring wavelength of 660 nm.

Then, the concentration of formed L-threonine in the sterilely filtered culture supernatant is determined with an amino-acid analyzer of the Eppendorf-BioTronik company (Hamburg, Germany) by ion exchange chromatography and postcolumn reaction with ninhydrin detection. The produced amount of threonine of one of the selected MG1655scr, AVH-resistance mutants is 2.15 g/l. No excretion of threonine can be demonstrated with the initial strain MG1655scr under these conditions. The mutant is designated by MG1655scrAHVR1.

Example 3

Cloning and Sequencing of the thrA Allele from MG1655scrAHVR1

The thrA allele from MG1655scrAHVR1 is amplified using the polymerase chain reaction (PCR) as well as synthetic oligonucleotides. Starting with the nucleotide sequence of the thrA gene in E. coli K12 MG1655 (accession number AE000111, Blattner et al. (Science 277: 1453-1462 (1997)), PCR primers are synthesized (MWG Biotech, Ebersberg, Germany).

ThrA1: 5'-ACCATTACCACCACCATCAC-3' (SEQ ID NO:5)

ThrA2: 5'-GCTCATATTGGCACTGGAAG-3' (SEQ ID NO:6)

The chromosomal MG1655scrAHVR1 DNA used for the PCR is isolated according to producer's instructions with QIAGEN genomic tips 100/G" (QIAGEN, Hilden, Germany). A DNA fragment approximately 2600 bp long can be amplified with the specific primers under standard PCR conditions (Innis et al.: PCR Protocols. A Guide to Methods and Applications, 1990, Academic Press) with Pfu-DNA polymerase (Promega Corporation, Madison, USA). The PCR product is cloned into the plasmid pCR-BluntII-TOPO and transformed into the E. coli strain TOP 10 (Invitrogen, Groningen, Netherlands, product description Zero Blunt TOPO PCR cloning kit, cat. No. K2800-20). Successful cloning is demonstrated by splitting the plasmid pCR-BluntAHVR1thrA with the restriction enzyme EcoRI. To this end the plasmid DNA is isolated by means of the "QIAprep spin plasmid kit" (QIAGEN, Hilden, Germany) and separated after the splitting in a 0.8% agarose gel. The DNA sequence of the amplified fragment is determined using the reverse and universal sequencing primer (QIAGEN, Hilden, Germany). The sequence of the thrA allele is shown in SEQ ID NO:3. The gene product or protein belonging to it is shown in SEQ ID NO:4.

What is claimed is:

1. An isolated polynucleotide which encodes a polypeptide having the amino acid sequence of SEQ ID NO: 2, wherein
   a) any proteinogenic amino acid except L-serine is present at position 345, and
   b) said polypeptide has aspartokinase I-homoserine dehydrogenase I enzymatic activity.

2. The isolated polynucleotide according to claim 1, wherein said proteinogenic amino acid at position 345 is L-phenylalanine, as shown in the amino acid sequence of SEQ ID NO: 4.

3. The isolated polynucleotide according to claim 1, wherein the polynucleotide comprises the nucleotide sequence of SEQ ID NO: 3, where thymidine is at position 1034 compared to SEQ ID NO: 1.

4. A plasmid or vector containing the polynucleotide according to claim 1.

5. The plasmid or vector according to claim 4 that replicates in Enterobacteriaceae.

6. An isolated bacterium mutant of the Enterobacteriaceae family which comprises a polynucleotide encoding a polypeptide having the amino acid sequence of SEQ ID NO: 2, and wherein
   a) any proteinogenic amino acid except L-serine is present at position 345, and
   b) said polypeptide has aspartokinase I-homoserine dehydrogenase I enzymatic activity.

7. An isolated bacterium mutant according to claim 6, wherein said proteinogenic amino acid at position 345 is phenylalanine.

8. The bacterium according to claim 6, wherein said polynucleotide is overexpressed.

9. The bacterium according to claim 6, wherein said bacterium mutant is of the species *E. coli*.

10. A recombinant bacterium of the Enterobacteriaceae family which has been transformed with the vector of claim 4.

11. A recombinant bacterium of the Enterobacteriaceae family which has been transformed with the vector of claim 5.

12. The recombinant bacterium according to claim 10, wherein said bacterium is of the species *E. coli*.

13. The recombinant bacterium according to claim 11, wherein said bacterium is of the species *E. coli*.

14. A method of producing L-threonine or a fodder additive containing L-threonine comprising the following steps:
   a) fermentation of a bacterium of the Enterobacteriaceae family consisting of an isolated polynucleotide which encodes a polypeptide comprising the amino acid sequence of SEQ ID NO: 2, wherein
      i) any proteinogenic amino acid except L-serine is present at position 345,
      ii) said polypeptide has aspartokinase I-homoserine dehydrogenase I enzymatic activity, and
   b) isolation of the L-threonine or fodder additive containing L-threonine from the fermentation broth.

15. The method according to claim 14, wherein said proteinogenic amino acid at position 345 is phenylalanine.

16. The method according to claim 14, wherein said isolated polynucleotide is overexpressed in a bacterium of Enterobacteriaceae family.

17. The method according to claim 14, wherein L-threonine is accumulated in the fermentation broth and then isolated from the fermentation broth.

18. The method according to claim 14, wherein L-threonine is accumulated in the fermentation broth and then isolated from the fermentation broth.

* * * * *

SEQUENCE LISTING

```
<160> NUMBER OF SEQ ID NOS: 6

<210> SEQ ID NO 1
<211> LENGTH: 2463
<212> TYPE: DNA
<213> ORGANISM: Escherichia coli
<220> FEATURE:
<221> NAME/KEY: CDS
<222> LOCATION: (1)..(2460)
<223> OTHER INFORMATION: thrA

<400> SEQUENCE: 1 atg cga gtg ttg aag ttc ggc ggt aca tca gtg gca aat gca gaa cgt       48
Met Arg Val Leu Lys Phe Gly Gly Thr Ser Val Ala Asn Ala Glu Arg
1               5                   10                  15 ttt ctg cgt gtt gcc gat att ctg gaa agc aat gcc agg cag ggg cag       96
Phe Leu Arg Val Ala Asp Ile Leu Glu Ser Asn Ala Arg Gln Gly Gln
                20                  25                  30 gtg gcc acc gtc ctc tct gcc ccc gcc aaa atc acc aac cac ctg gtg      144
Val Ala Thr Val Leu Ser Ala Pro Ala Lys Ile Thr Asn His Leu Val
            35                  40                  45 gcg atg att gaa aaa acc att agc ggc cag gat gct tta ccc aat atc      192
Ala Met Ile Glu Lys Thr Ile Ser Gly Gln Asp Ala Leu Pro Asn Ile
        50                  55                  60 agc gat gcc gaa cgt att ttt gcc gaa ctt ttg acg gga ctc gcc gcc      240
Ser Asp Ala Glu Arg Ile Phe Ala Glu Leu Leu Thr Gly Leu Ala Ala
65                  70                  75                  80 gcc cag ccg ggg ttc ccg ctg gcg caa ttg aaa act ttc gtc gat cag      288
Ala Gln Pro Gly Phe Pro Leu Ala Gln Leu Lys Thr Phe Val Asp Gln
                85                  90                  95
```

-continued

```
gaa ttt gcc caa ata aaa cat gtc ctg cat ggc att agt ttg ttg ggg        336
Glu Phe Ala Gln Ile Lys His Val Leu His Gly Ile Ser Leu Leu Gly
            100                 105                 110 cag tgc ccg gat agc atc aac gct gcg ctg att tgc cgt ggc gag aaa        384
Gln Cys Pro Asp Ser Ile Asn Ala Ala Leu Ile Cys Arg Gly Glu Lys
        115                 120                 125 atg tcg atc gcc att atg gcc ggc gta tta gaa gcg cgc ggt cac aac        432
Met Ser Ile Ala Ile Met Ala Gly Val Leu Glu Ala Arg Gly His Asn
130                 135                 140 gtt act gtt atc gat ccg gtc gaa aaa ctg ctg gca gtg ggg cat tac        480
Val Thr Val Ile Asp Pro Val Glu Lys Leu Leu Ala Val Gly His Tyr
145                 150                 155                 160 ctc gaa tct acc gtc gat att gct gag tcc acc cgc cgt att gcg gca        528
Leu Glu Ser Thr Val Asp Ile Ala Glu Ser Thr Arg Arg Ile Ala Ala
                165                 170                 175 agc cgc att ccg gct gat cac atg gtg ctg atg gca ggt ttc acc gcc        576
Ser Arg Ile Pro Ala Asp His Met Val Leu Met Ala Gly Phe Thr Ala
            180                 185                 190 ggt aat gaa aaa ggc gaa ctg gtg gtg ctt gga cgc aac ggt tcc gac        624
Gly Asn Glu Lys Gly Glu Leu Val Val Leu Gly Arg Asn Gly Ser Asp
        195                 200                 205 tac tct gct gcg gtg ctg gct gcc tgt tta cgc gcc gat tgt tgc gag        672
Tyr Ser Ala Ala Val Leu Ala Ala Cys Leu Arg Ala Asp Cys Cys Glu
210                 215                 220 att tgg acg gac gtt gac ggg gtc tat acc tgc gac ccg cgt cag gtg        720
Ile Trp Thr Asp Val Asp Gly Val Tyr Thr Cys Asp Pro Arg Gln Val
225                 230                 235                 240 ccc gat gcg agg ttg ttg aag tcg atg tcc tac cag gaa gcg atg gag        768
Pro Asp Ala Arg Leu Leu Lys Ser Met Ser Tyr Gln Glu Ala Met Glu
                245                 250                 255 ctt tcc tac ttc ggc gct aaa gtt ctt cac ccc cgc acc att acc ccc        816
Leu Ser Tyr Phe Gly Ala Lys Val Leu His Pro Arg Thr Ile Thr Pro
            260                 265                 270 atc gcc cag ttc cag atc cct tgc ctg att aaa aat acc gga aat cct        864
Ile Ala Gln Phe Gln Ile Pro Cys Leu Ile Lys Asn Thr Gly Asn Pro
        275                 280                 285 caa gca cca ggt acg ctc att ggt gcc agc cgt gat gaa gac gaa tta        912
Gln Ala Pro Gly Thr Leu Ile Gly Ala Ser Arg Asp Glu Asp Glu Leu
290                 295                 300 ccg gtc aag ggc att tcc aat ctg aat aac atg gca atg ttc agc gtt        960
Pro Val Lys Gly Ile Ser Asn Leu Asn Asn Met Ala Met Phe Ser Val
305                 310                 315                 320 tct ggt ccg ggg atg aaa ggg atg gtc ggc atg gcg gcg cgc gtc ttt       1008
Ser Gly Pro Gly Met Lys Gly Met Val Gly Met Ala Ala Arg Val Phe
                325                 330                 335 gca gcg atg tca cgc gcc cgt att tcc gtg gtg ctg att acg caa tca       1056
Ala Ala Met Ser Arg Ala Arg Ile Ser Val Val Leu Ile Thr Gln Ser
            340                 345                 350 tct tcc gaa tac agc atc agt ttc tgc gtt cca caa agc gac tgt gtg       1104
Ser Ser Glu Tyr Ser Ile Ser Phe Cys Val Pro Gln Ser Asp Cys Val
        355                 360                 365 cga gct gaa cgg gca atg cag gaa gag ttc tac ctg gaa ctg aaa gaa       1152
Arg Ala Glu Arg Ala Met Gln Glu Glu Phe Tyr Leu Glu Leu Lys Glu
370                 375                 380 ggc tta ctg gag ccg ctg gca gtg acg gaa cgg ctg gcc att atc tcg       1200
Gly Leu Leu Glu Pro Leu Ala Val Thr Glu Arg Leu Ala Ile Ile Ser
385                 390                 395                 400 gtg gta ggt gat ggt atg cgc acc ttg cgt ggg atc tcg gcg aaa ttc       1248
Val Val Gly Asp Gly Met Arg Thr Leu Arg Gly Ile Ser Ala Lys Phe
                405                 410                 415
```

-continued

| | |
|---|---|
| ttt gcc gca ctg gcc cgc gcc aat atc aac att gtc gcc att gct cag<br>Phe Ala Ala Leu Ala Arg Ala Asn Ile Asn Ile Val Ala Ile Ala Gln<br>420                           425                         430 | 1296 |
| gga tct tct gaa cgc tca atc tct gtc gtg gta aat aac gat gat gcg<br>Gly Ser Ser Glu Arg Ser Ile Ser Val Val Val Asn Asn Asp Asp Ala<br>             435                         440                       445 | 1344 |
| acc act ggc gtg cgc gtt act cat cag atg ctg ttc aat acc gat cag<br>Thr Thr Gly Val Arg Val Thr His Gln Met Leu Phe Asn Thr Asp Gln<br>450                           455                         460 | 1392 |
| gtt atc gaa gtg ttt gtg att ggc gtc ggt ggc gtt ggc ggt gcg ctg<br>Val Ile Glu Val Phe Val Ile Gly Val Gly Gly Val Gly Gly Ala Leu<br>465                           470                       475                     480 | 1440 |
| ctg gag caa ctg aag cgt cag caa agc tgg ctg aag aat aaa cat atc<br>Leu Glu Gln Leu Lys Arg Gln Gln Ser Trp Leu Lys Asn Lys His Ile<br>                     485                       490                       495 | 1488 |
| gac tta cgt gtc tgc ggt gtt gcc aac tcg aag gct ctg ctc acc aat<br>Asp Leu Arg Val Cys Gly Val Ala Asn Ser Lys Ala Leu Leu Thr Asn<br>                         500                       505                   510 | 1536 |
| gta cat ggc ctt aat ctg gaa aac tgg cag gaa gaa ctg gcg caa gcc<br>Val His Gly Leu Asn Leu Glu Asn Trp Gln Glu Glu Leu Ala Gln Ala<br>        515                       520                       525 | 1584 |
| aaa gag ccg ttt aat ctc ggg cgc tta att cgc ctc gtg aaa gaa tat<br>Lys Glu Pro Phe Asn Leu Gly Arg Leu Ile Arg Leu Val Lys Glu Tyr<br>530                           535                       540 | 1632 |
| cat ctg ctg aac ccg gtc att gtt gac tgc act tcc agc cag gca gtg<br>His Leu Leu Asn Pro Val Ile Val Asp Cys Thr Ser Ser Gln Ala Val<br>545                           550                       555                   560 | 1680 |
| gcg gat caa tat gcc gac ttc ctg cgc gaa ggt ttc cac gtt gtc acg<br>Ala Asp Gln Tyr Ala Asp Phe Leu Arg Glu Gly Phe His Val Val Thr<br>                     565                       570                       575 | 1728 |
| ccg aac aaa aag gcc aac acc tcg tcg atg gat tac tac cat cag ttg<br>Pro Asn Lys Lys Ala Asn Thr Ser Ser Met Asp Tyr Tyr His Gln Leu<br>                  580                       585                       590 | 1776 |
| cgt tat gcg gcg gaa aaa tcg cgg cgt aaa ttc ctc tat gac acc aac<br>Arg Tyr Ala Ala Glu Lys Ser Arg Arg Lys Phe Leu Tyr Asp Thr Asn<br>        595                       600                       605 | 1824 |
| gtt ggg gct gga tta ccg gtt att gag aac ctg caa aat ctg ctc aat<br>Val Gly Ala Gly Leu Pro Val Ile Glu Asn Leu Gln Asn Leu Leu Asn<br>610                           615                       620 | 1872 |
| gca ggt gat gaa ttg atg aag ttc tcc ggc att ctt tct ggt tcg ctt<br>Ala Gly Asp Glu Leu Met Lys Phe Ser Gly Ile Leu Ser Gly Ser Leu<br>625                           630                       635                   640 | 1920 |
| tct tat atc ttc ggc aag tta gac gaa ggc atg agt ttc tcc gag gcg<br>Ser Tyr Ile Phe Gly Lys Leu Asp Glu Gly Met Ser Phe Ser Glu Ala<br>                   645                       650                   655 | 1968 |
| acc acg ctg gcg cgg gaa atg ggt tat acc gaa ccg gac ccg cga gat<br>Thr Thr Leu Ala Arg Glu Met Gly Tyr Thr Glu Pro Asp Pro Arg Asp<br>             660                         665                       670 | 2016 |
| gat ctt tct ggt atg gat gtg gcg cgt aaa cta ttg att ctc gct cgt<br>Asp Leu Ser Gly Met Asp Val Ala Arg Lys Leu Leu Ile Leu Ala Arg<br>675                           680                       685 | 2064 |
| gaa acg gga cgt gaa ctg gag ctg gcg gat att gaa att gaa cct gtg<br>Glu Thr Gly Arg Glu Leu Glu Leu Ala Asp Ile Glu Ile Glu Pro Val<br>690                           695                       700 | 2112 |
| ctg ccc gca gag ttt aac gcc gag ggt gat gtt gcc gct ttt atg gcg<br>Leu Pro Ala Glu Phe Asn Ala Glu Gly Asp Val Ala Ala Phe Met Ala<br>705                           710                       715                   720 | 2160 |
| aat ctg tca caa ctc gac gat ctc ttt gcc gcg cgc gtg gcg aag gcc<br>Asn Leu Ser Gln Leu Asp Asp Leu Phe Ala Ala Arg Val Ala Lys Ala<br>                         725                       730                   735 | 2208 |

```
cgt gat gaa gga aaa gtt ttg cgc tat gtt ggc aat att gat gaa gat    2256
Arg Asp Glu Gly Lys Val Leu Arg Tyr Val Gly Asn Ile Asp Glu Asp
            740                 745                 750 ggc gtc tgc cgc gtg aag att gcc gaa gtg gat ggt aat gat ccg ctg    2304
Gly Val Cys Arg Val Lys Ile Ala Glu Val Asp Gly Asn Asp Pro Leu
            755                 760                 765 ttc aaa gtg aaa aat ggc gaa aac gcc ctg gcc ttc tat agc cac tat    2352
Phe Lys Val Lys Asn Gly Glu Asn Ala Leu Ala Phe Tyr Ser His Tyr
            770                 775                 780 tat cag ccg ctg ccg ttg gta ctg cgc gga tat ggt gcg ggc aat gac    2400
Tyr Gln Pro Leu Pro Leu Val Leu Arg Gly Tyr Gly Ala Gly Asn Asp
785                 790                 795                 800 gtt aca gct gcc ggt gtc ttt gct gat ctg cta cgt acc ctc tca tgg    2448
Val Thr Ala Ala Gly Val Phe Ala Asp Leu Leu Arg Thr Leu Ser Trp
                805                 810                 815 aag tta gga gtc tga                                                2463
Lys Leu Gly Val
                820

<210> SEQ ID NO 2
<211> LENGTH: 820
<212> TYPE: PRT
<213> ORGANISM: Escherichia coli

<400> SEQUENCE: 2

Met Arg Val Leu Lys Phe Gly Gly Thr Ser Val Ala Asn Ala Glu Arg
1               5                   10                  15

Phe Leu Arg Val Ala Asp Ile Leu Glu Ser Asn Ala Arg Gln Gly Gln
            20                  25                  30

Val Ala Thr Val Leu Ser Ala Pro Ala Lys Ile Thr Asn His Leu Val
        35                  40                  45

Ala Met Ile Glu Lys Thr Ile Ser Gly Gln Asp Ala Leu Pro Asn Ile
    50                  55                  60

Ser Asp Ala Glu Arg Ile Phe Ala Glu Leu Leu Thr Gly Leu Ala Ala
65                  70                  75                  80

Ala Gln Pro Gly Phe Pro Leu Ala Gln Leu Lys Thr Phe Val Asp Gln
                85                  90                  95

Glu Phe Ala Gln Ile Lys His Val Leu His Gly Ile Ser Leu Leu Gly
            100                 105                 110

Gln Cys Pro Asp Ser Ile Asn Ala Ala Leu Ile Cys Arg Gly Glu Lys
        115                 120                 125

Met Ser Ile Ala Ile Met Ala Gly Val Leu Glu Ala Arg Gly His Asn
    130                 135                 140

Val Thr Val Ile Asp Pro Val Glu Lys Leu Leu Ala Val Gly His Tyr
145                 150                 155                 160

Leu Glu Ser Thr Val Asp Ile Ala Glu Ser Thr Arg Arg Ile Ala Ala
                165                 170                 175

Ser Arg Ile Pro Ala Asp His Met Val Leu Met Ala Gly Phe Thr Ala
            180                 185                 190

Gly Asn Glu Lys Gly Glu Leu Val Val Leu Gly Arg Asn Gly Ser Asp
        195                 200                 205

Tyr Ser Ala Ala Val Leu Ala Ala Cys Leu Arg Ala Asp Cys Cys Glu
    210                 215                 220

Ile Trp Thr Asp Val Asp Gly Val Tyr Thr Cys Asp Pro Arg Gln Val
225                 230                 235                 240

Pro Asp Ala Arg Leu Leu Lys Ser Met Ser Tyr Gln Glu Ala Met Glu
                245                 250                 255
```

-continued

```
Leu Ser Tyr Phe Gly Ala Lys Val Leu His Pro Arg Thr Ile Thr Pro
            260                 265                 270

Ile Ala Gln Phe Gln Ile Pro Cys Leu Ile Lys Asn Thr Gly Asn Pro
        275                 280                 285

Gln Ala Pro Gly Thr Leu Ile Gly Ala Ser Arg Asp Glu Asp Glu Leu
    290                 295                 300

Pro Val Lys Gly Ile Ser Asn Leu Asn Asn Met Ala Met Phe Ser Val
305                 310                 315                 320

Ser Gly Pro Gly Met Lys Gly Met Val Gly Met Ala Ala Arg Val Phe
                325                 330                 335

Ala Ala Met Ser Arg Ala Arg Ile Ser Val Val Leu Ile Thr Gln Ser
            340                 345                 350

Ser Ser Glu Tyr Ser Ile Ser Phe Cys Val Pro Gln Ser Asp Cys Val
        355                 360                 365

Arg Ala Glu Arg Ala Met Gln Glu Glu Phe Tyr Leu Glu Leu Lys Glu
    370                 375                 380

Gly Leu Leu Glu Pro Leu Ala Val Thr Glu Arg Leu Ala Ile Ile Ser
385                 390                 395                 400

Val Val Gly Asp Gly Met Arg Thr Leu Arg Gly Ile Ser Ala Lys Phe
                405                 410                 415

Phe Ala Ala Leu Ala Arg Ala Asn Ile Asn Ile Val Ala Ile Ala Gln
            420                 425                 430

Gly Ser Ser Glu Arg Ser Ile Ser Val Val Val Asn Asn Asp Asp Ala
        435                 440                 445

Thr Thr Gly Val Arg Val Thr His Gln Met Leu Phe Asn Thr Asp Gln
    450                 455                 460

Val Ile Glu Val Phe Val Ile Gly Val Gly Val Gly Gly Ala Leu
465                 470                 475                 480

Leu Glu Gln Leu Lys Arg Gln Gln Ser Trp Leu Lys Asn Lys His Ile
                485                 490                 495

Asp Leu Arg Val Cys Gly Val Ala Asn Ser Lys Ala Leu Leu Thr Asn
            500                 505                 510

Val His Gly Leu Asn Leu Glu Asn Trp Gln Glu Glu Leu Ala Gln Ala
        515                 520                 525

Lys Glu Pro Phe Asn Leu Gly Arg Leu Ile Arg Leu Val Lys Glu Tyr
    530                 535                 540

His Leu Leu Asn Pro Val Ile Val Asp Cys Thr Ser Ser Gln Ala Val
545                 550                 555                 560

Ala Asp Gln Tyr Ala Asp Phe Leu Arg Glu Gly Phe His Val Val Thr
                565                 570                 575

Pro Asn Lys Lys Ala Asn Thr Ser Ser Met Asp Tyr Tyr His Gln Leu
            580                 585                 590

Arg Tyr Ala Ala Glu Lys Ser Arg Arg Lys Phe Leu Tyr Asp Thr Asn
        595                 600                 605

Val Gly Ala Gly Leu Pro Val Ile Glu Asn Leu Gln Asn Leu Leu Asn
    610                 615                 620

Ala Gly Asp Glu Leu Met Lys Phe Ser Gly Ile Leu Ser Gly Ser Leu
625                 630                 635                 640

Ser Tyr Ile Phe Gly Lys Leu Asp Glu Gly Met Ser Phe Ser Glu Ala
                645                 650                 655

Thr Thr Leu Ala Arg Glu Met Gly Tyr Thr Glu Pro Asp Pro Arg Asp
            660                 665                 670

Asp Leu Ser Gly Met Asp Val Ala Arg Lys Leu Leu Ile Leu Ala Arg
        675                 680                 685
```

-continued

```
Glu Thr Gly Arg Glu Leu Glu Leu Ala Asp Ile Glu Ile Glu Pro Val
    690                 695                 700
Leu Pro Ala Glu Phe Asn Ala Glu Gly Asp Val Ala Ala Phe Met Ala
705                 710                 715                 720
Asn Leu Ser Gln Leu Asp Asp Leu Phe Ala Ala Arg Val Ala Lys Ala
                725                 730                 735
Arg Asp Glu Gly Lys Val Leu Arg Tyr Val Gly Asn Ile Asp Glu Asp
            740                 745                 750
Gly Val Cys Arg Val Lys Ile Ala Glu Val Asp Gly Asn Asp Pro Leu
        755                 760                 765
Phe Lys Val Lys Asn Gly Glu Asn Ala Leu Ala Phe Tyr Ser His Tyr
    770                 775                 780
Tyr Gln Pro Leu Pro Leu Val Leu Arg Gly Tyr Gly Ala Gly Asn Asp
785                 790                 795                 800
Val Thr Ala Ala Gly Val Phe Ala Asp Leu Leu Arg Thr Leu Ser Trp
                805                 810                 815
Lys Leu Gly Val
            820
```

<210> SEQ ID NO 3
<211> LENGTH: 2463
<212> TYPE: DNA
<213> ORGANISM: Escherichia coli
<220> FEATURE:
<221> NAME/KEY: CDS
<222> LOCATION: (1)..(2460)
<223> OTHER INFORMATION: thrA

<400> SEQUENCE: 3

```
atg cga gtg ttg aag ttc ggc ggt aca tca gtg gca aat gca gaa cgt    48
Met Arg Val Leu Lys Phe Gly Gly Thr Ser Val Ala Asn Ala Glu Arg
1               5                   10                  15 ttt ctg cgt gtt gcc gat att ctg gaa agc aat gcc agg cag ggg cag    96
Phe Leu Arg Val Ala Asp Ile Leu Glu Ser Asn Ala Arg Gln Gly Gln
                20                  25                  30 gtg gcc acc gtc ctc tct gcc ccc gcc aaa atc acc aac cac ctg gtg   144
Val Ala Thr Val Leu Ser Ala Pro Ala Lys Ile Thr Asn His Leu Val
            35                  40                  45 gcg atg att gaa aaa acc att agc ggc cag gat gct tta ccc aat atc   192
Ala Met Ile Glu Lys Thr Ile Ser Gly Gln Asp Ala Leu Pro Asn Ile
        50                  55                  60 agc gat gcc gaa cgt att ttt gcc gaa ctt ttg acg gga ctc gcc gcc   240
Ser Asp Ala Glu Arg Ile Phe Ala Glu Leu Leu Thr Gly Leu Ala Ala
65                  70                  75                  80 gcc cag ccg ggg ttc ccg ctg gcg caa ttg aaa act ttc gtc gat cag   288
Ala Gln Pro Gly Phe Pro Leu Ala Gln Leu Lys Thr Phe Val Asp Gln
                85                  90                  95 gaa ttt gcc caa ata aaa cat gtc ctg cat ggc att agt ttg ttg ggg   336
Glu Phe Ala Gln Ile Lys His Val Leu His Gly Ile Ser Leu Leu Gly
                100                 105                 110 cag tgc ccg gat agc atc aac gct gcg ctg att tgc cgt ggc gag aaa   384
Gln Cys Pro Asp Ser Ile Asn Ala Ala Leu Ile Cys Arg Gly Glu Lys
            115                 120                 125 atg tcg atc gcc att atg gcc ggc gta tta gaa gcg cgc ggt cac aac   432
Met Ser Ile Ala Ile Met Ala Gly Val Leu Glu Ala Arg Gly His Asn
        130                 135                 140 gtt act gtt atc gat ccg gtc gaa aaa ctg ctg gca gtg ggg cat tac   480
Val Thr Val Ile Asp Pro Val Glu Lys Leu Leu Ala Val Gly His Tyr
145                 150                 155                 160
```

-continued

| | |
|---|---|
| ctc gaa tct acc gtc gat att gct gag tcc acc cgc cgt att gcg gca<br>Leu Glu Ser Thr Val Asp Ile Ala Glu Ser Thr Arg Arg Ile Ala Ala<br>                    165                              170                        175 | 528 |
| agc cgc att ccg gct gat cac atg gtg ctg atg gca ggt ttc acc gcc<br>Ser Arg Ile Pro Ala Asp His Met Val Leu Met Ala Gly Phe Thr Ala<br>        180                              185                            190 | 576 |
| ggt aat gaa aaa ggc gaa ctg gtg gtg ctt gga cgc aac ggt tcc gac<br>Gly Asn Glu Lys Gly Glu Leu Val Val Leu Gly Arg Asn Gly Ser Asp<br>            195                            200                        205 | 624 |
| tac tct gct gcg gtg ctg gct gcc tgt tta cgc gcc gat tgt tgc gag<br>Tyr Ser Ala Ala Val Leu Ala Ala Cys Leu Arg Ala Asp Cys Cys Glu<br>    210                            215                        220 | 672 |
| att tgg acg gac gtt gac ggg gtc tat acc tgc gac ccg cgt cag gtg<br>Ile Trp Thr Asp Val Asp Gly Val Tyr Thr Cys Asp Pro Arg Gln Val<br>225                      230                        235                        240 | 720 |
| ccc gat gcg agg ttg ttg aag tcg atg tcc tac cag gaa gcg atg gag<br>Pro Asp Ala Arg Leu Leu Lys Ser Met Ser Tyr Gln Glu Ala Met Glu<br>                    245                              250                        255 | 768 |
| ctt tcc tac ttc ggc gct aaa gtt ctt cac ccc cgc acc att acc ccc<br>Leu Ser Tyr Phe Gly Ala Lys Val Leu His Pro Arg Thr Ile Thr Pro<br>        260                              265                            270 | 816 |
| atc gcc cag ttc cag atc cct tgc ctg att aaa aat acc gga aat cct<br>Ile Ala Gln Phe Gln Ile Pro Cys Leu Ile Lys Asn Thr Gly Asn Pro<br>            275                            280                        285 | 864 |
| caa gca cca ggt acg ctc att ggt gcc agc cgt gat gaa gac gaa tta<br>Gln Ala Pro Gly Thr Leu Ile Gly Ala Ser Arg Asp Glu Asp Glu Leu<br>    290                            295                        300 | 912 |
| ccg gtc aag ggc att tcc aat ctg aat aac atg gca atg ttc agc gtt<br>Pro Val Lys Gly Ile Ser Asn Leu Asn Asn Met Ala Met Phe Ser Val<br>305                      310                        315                        320 | 960 |
| tct ggt ccg ggg atg aaa ggg atg gtc ggc atg gcg gcg cgc gtc ttt<br>Ser Gly Pro Gly Met Lys Gly Met Val Gly Met Ala Ala Arg Val Phe<br>                    325                              330                        335 | 1008 |
| gca gcg atg tca cgc gcc cgt att ttc gtg gtg ctg att acg caa tca<br>Ala Ala Met Ser Arg Ala Arg Ile Phe Val Val Leu Ile Thr Gln Ser<br>        340                              345                            350 | 1056 |
| tct tcc gaa tac agc atc agt ttc tgc gtt cca caa agc gac tgt gtg<br>Ser Ser Glu Tyr Ser Ile Ser Phe Cys Val Pro Gln Ser Asp Cys Val<br>            355                            360                        365 | 1104 |
| cga gct gaa cgg gca atg cag gaa gag ttc tac ctg gaa ctg aaa gaa<br>Arg Ala Glu Arg Ala Met Gln Glu Glu Phe Tyr Leu Glu Leu Lys Glu<br>    370                            375                        380 | 1152 |
| ggc tta ctg gag ccg ctg gca gtg acg gaa cgg ctg gcc att atc tcg<br>Gly Leu Leu Glu Pro Leu Ala Val Thr Glu Arg Leu Ala Ile Ile Ser<br>385                      390                        395                        400 | 1200 |
| gtg gta ggt gat ggt atg cgc acc ttg cgt ggg atc tcg gcg aaa ttc<br>Val Val Gly Asp Gly Met Arg Thr Leu Arg Gly Ile Ser Ala Lys Phe<br>                    405                              410                        415 | 1248 |
| ttt gcc gca ctg gcc cgc gcc aat atc aac att gtc gcc att gct cag<br>Phe Ala Ala Leu Ala Arg Ala Asn Ile Asn Ile Val Ala Ile Ala Gln<br>        420                              425                            430 | 1296 |
| gga tct tct gaa cgc tca atc tct gtc gtg gta aat aac gat gat gcg<br>Gly Ser Ser Glu Arg Ser Ile Ser Val Val Val Asn Asn Asp Asp Ala<br>            435                            440                        445 | 1344 |
| acc act ggc gtg cgc gtt act cat cag atg ctg ttc aat acc gat cag<br>Thr Thr Gly Val Arg Val Thr His Gln Met Leu Phe Asn Thr Asp Gln<br>    450                            455                        460 | 1392 |
| gtt atc gaa gtg ttt gtg att ggc gtc ggt ggc gtt ggc ggt gcg ctg<br>Val Ile Glu Val Phe Val Ile Gly Val Gly Gly Val Gly Gly Ala Leu<br>465                      470                        475                        480 | 1440 |

```
ctg gag caa ctg aag cgt cag caa agc tgg ctg aag aat aaa cat atc    1488
Leu Glu Gln Leu Lys Arg Gln Gln Ser Trp Leu Lys Asn Lys His Ile
                485                 490                 495 gac tta cgt gtc tgc ggt gtt gcc aac tcg aag gct ctg ctc acc aat    1536
Asp Leu Arg Val Cys Gly Val Ala Asn Ser Lys Ala Leu Leu Thr Asn
            500                 505                 510 gta cat ggc ctt aat ctg gaa aac tgg cag gaa gaa ctg gcg caa gcc    1584
Val His Gly Leu Asn Leu Glu Asn Trp Gln Glu Glu Leu Ala Gln Ala
        515                 520                 525 aaa gag ccg ttt aat ctc ggg cgc tta att cgc ctc gtg aaa gaa tat    1632
Lys Glu Pro Phe Asn Leu Gly Arg Leu Ile Arg Leu Val Lys Glu Tyr
    530                 535                 540 cat ctg ctg aac ccg gtc att gtt gac tgc act tcc agc cag gca gtg    1680
His Leu Leu Asn Pro Val Ile Val Asp Cys Thr Ser Ser Gln Ala Val
545                 550                 555                 560 gcg gat caa tat gcc gac ttc ctg cgc gaa ggt ttc cac gtt gtc acg    1728
Ala Asp Gln Tyr Ala Asp Phe Leu Arg Glu Gly Phe His Val Val Thr
                565                 570                 575 ccg aac aaa aag gcc aac acc tcg tcg atg gat tac tac cat cag ttg    1776
Pro Asn Lys Lys Ala Asn Thr Ser Ser Met Asp Tyr Tyr His Gln Leu
            580                 585                 590 cgt tat gcg gcg gaa aaa tcg cgg cgt aaa ttc ctc tat gac acc aac    1824
Arg Tyr Ala Ala Glu Lys Ser Arg Arg Lys Phe Leu Tyr Asp Thr Asn
        595                 600                 605 gtt ggg gct gga tta ccg gtt att gag aac ctg caa aat ctg ctc aat    1872
Val Gly Ala Gly Leu Pro Val Ile Glu Asn Leu Gln Asn Leu Leu Asn
    610                 615                 620 gca ggt gat gaa ttg atg aag ttc tcc ggc att ctt tct ggt tcg ctt    1920
Ala Gly Asp Glu Leu Met Lys Phe Ser Gly Ile Leu Ser Gly Ser Leu
625                 630                 635                 640 tct tat atc ttc ggc aag tta gac gaa ggc atg agt ttc tcc gag gcg    1968
Ser Tyr Ile Phe Gly Lys Leu Asp Glu Gly Met Ser Phe Ser Glu Ala
                645                 650                 655 acc acg ctg gcg cgg gaa atg ggt tat acc gaa ccg gac ccg cga gat    2016
Thr Thr Leu Ala Arg Glu Met Gly Tyr Thr Glu Pro Asp Pro Arg Asp
            660                 665                 670 gat ctt tct ggt atg gat gtg gcg cgt aaa cta ttg att ctc gct cgt    2064
Asp Leu Ser Gly Met Asp Val Ala Arg Lys Leu Leu Ile Leu Ala Arg
        675                 680                 685 gaa acg gga cgt gaa ctg gag ctg gcg gat att gaa att gaa cct gtg    2112
Glu Thr Gly Arg Glu Leu Glu Leu Ala Asp Ile Glu Ile Glu Pro Val
    690                 695                 700 ctg ccc gca gag ttt aac gcc gag ggt gat gtt gcc gct ttt atg gcg    2160
Leu Pro Ala Glu Phe Asn Ala Glu Gly Asp Val Ala Ala Phe Met Ala
705                 710                 715                 720 aat ctg tca caa ctc gac gat ctc ttt gcc gcg cgc gtg gcg aag gcc    2208
Asn Leu Ser Gln Leu Asp Asp Leu Phe Ala Ala Arg Val Ala Lys Ala
                725                 730                 735 cgt gat gaa gga aaa gtt ttg cgc tat gtt ggc aat att gat gaa gat    2256
Arg Asp Glu Gly Lys Val Leu Arg Tyr Val Gly Asn Ile Asp Glu Asp
            740                 745                 750 ggc gtc tgc cgc gtg aag att gcc gaa gtg gat ggt aat gat ccg ctg    2304
Gly Val Cys Arg Val Lys Ile Ala Glu Val Asp Gly Asn Asp Pro Leu
        755                 760                 765 ttc aaa gtg aaa aat ggc gaa aac gcc ctg gcc ttc tat agc cac tat    2352
Phe Lys Val Lys Asn Gly Glu Asn Ala Leu Ala Phe Tyr Ser His Tyr
    770                 775                 780 tat cag ccg ctg ccg ttg gta ctg cgc gga tat ggt gcg ggc aat gac    2400
Tyr Gln Pro Leu Pro Leu Val Leu Arg Gly Tyr Gly Ala Gly Asn Asp
785                 790                 795                 800
```

```
gtt aca gct gcc ggt gtc ttt gct gat ctg cta cgt acc ctc tca tgg    2448
Val Thr Ala Ala Gly Val Phe Ala Asp Leu Leu Arg Thr Leu Ser Trp
            805                 810                 815 aag tta gga gtc tga                                                 2463
Lys Leu Gly Val
        820

<210> SEQ ID NO 4
<211> LENGTH: 820
<212> TYPE: PRT
<213> ORGANISM: Escherichia coli

<400> SEQUENCE: 4
```

Met Arg Val Leu Lys Phe Gly Gly Thr Ser Val Ala Asn Ala Glu Arg
1               5                   10                  15

Phe Leu Arg Val Ala Asp Ile Leu Glu Ser Asn Ala Arg Gln Gly Gln
            20                  25                  30

Val Ala Thr Val Leu Ser Ala Pro Ala Lys Ile Thr Asn His Leu Val
        35                  40                  45

Ala Met Ile Glu Lys Thr Ile Ser Gly Gln Asp Ala Leu Pro Asn Ile
    50                  55                  60

Ser Asp Ala Glu Arg Ile Phe Ala Glu Leu Leu Thr Gly Leu Ala Ala
65                  70                  75                  80

Ala Gln Pro Gly Phe Pro Leu Ala Gln Leu Lys Thr Phe Val Asp Gln
                85                  90                  95

Glu Phe Ala Gln Ile Lys His Val Leu His Gly Ile Ser Leu Leu Gly
            100                 105                 110

Gln Cys Pro Asp Ser Ile Asn Ala Ala Leu Ile Cys Arg Gly Glu Lys
        115                 120                 125

Met Ser Ile Ala Ile Met Ala Gly Val Leu Glu Ala Arg Gly His Asn
    130                 135                 140

Val Thr Val Ile Asp Pro Val Glu Lys Leu Leu Ala Val Gly His Tyr
145                 150                 155                 160

Leu Glu Ser Thr Val Asp Ile Ala Glu Ser Thr Arg Arg Ile Ala Ala
                165                 170                 175

Ser Arg Ile Pro Ala Asp His Met Val Leu Met Ala Gly Phe Thr Ala
            180                 185                 190

Gly Asn Glu Lys Gly Glu Leu Val Val Leu Gly Arg Asn Gly Ser Asp
        195                 200                 205

Tyr Ser Ala Ala Val Leu Ala Ala Cys Leu Arg Ala Asp Cys Cys Glu
    210                 215                 220

Ile Trp Thr Asp Val Asp Gly Val Tyr Thr Cys Asp Pro Arg Gln Val
225                 230                 235                 240

Pro Asp Ala Arg Leu Leu Lys Ser Met Ser Tyr Gln Glu Ala Met Glu
                245                 250                 255

Leu Ser Tyr Phe Gly Ala Lys Val Leu His Pro Arg Thr Ile Thr Pro
            260                 265                 270

Ile Ala Gln Phe Gln Ile Pro Cys Leu Ile Lys Asn Thr Gly Asn Pro
        275                 280                 285

Gln Ala Pro Gly Thr Leu Ile Gly Ala Ser Arg Asp Glu Asp Glu Leu
    290                 295                 300

Pro Val Lys Gly Ile Ser Asn Leu Asn Asn Met Ala Met Phe Ser Val
305                 310                 315                 320

Ser Gly Pro Gly Met Lys Gly Met Val Gly Met Ala Ala Arg Val Phe
                325                 330                 335

Ala Ala Met Ser Arg Ala Arg Ile Phe Val Val Leu Ile Thr Gln Ser

```
                    340                 345                 350
Ser Ser Glu Tyr Ser Ile Ser Phe Cys Val Pro Gln Ser Asp Cys Val
        355                 360                 365

Arg Ala Glu Arg Ala Met Gln Glu Glu Phe Tyr Leu Glu Leu Lys Glu
        370                 375                 380

Gly Leu Leu Glu Pro Leu Ala Val Thr Glu Arg Leu Ala Ile Ile Ser
385                 390                 395                 400

Val Val Gly Asp Gly Met Arg Thr Leu Arg Gly Ile Ser Ala Lys Phe
                405                 410                 415

Phe Ala Ala Leu Ala Arg Ala Asn Ile Asn Ile Val Ala Ile Ala Gln
                420                 425                 430

Gly Ser Ser Glu Arg Ser Ile Ser Val Val Asn Asn Asp Asp Ala
        435                 440                 445

Thr Thr Gly Val Arg Val Thr His Gln Met Leu Phe Asn Thr Asp Gln
        450                 455                 460

Val Ile Glu Val Phe Val Ile Gly Val Gly Gly Val Gly Gly Ala Leu
465                 470                 475                 480

Leu Glu Gln Leu Lys Arg Gln Gln Ser Trp Leu Lys Asn Lys His Ile
                485                 490                 495

Asp Leu Arg Val Cys Gly Val Ala Asn Ser Lys Ala Leu Leu Thr Asn
                500                 505                 510

Val His Gly Leu Asn Leu Glu Asn Trp Gln Glu Glu Leu Ala Gln Ala
        515                 520                 525

Lys Glu Pro Phe Asn Leu Gly Arg Leu Ile Arg Leu Val Lys Glu Tyr
        530                 535                 540

His Leu Leu Asn Pro Val Ile Val Asp Cys Thr Ser Ser Gln Ala Val
545                 550                 555                 560

Ala Asp Gln Tyr Ala Asp Phe Leu Arg Glu Gly Phe His Val Val Thr
                565                 570                 575

Pro Asn Lys Lys Ala Asn Thr Ser Ser Met Asp Tyr Tyr His Gln Leu
                580                 585                 590

Arg Tyr Ala Ala Glu Lys Ser Arg Arg Lys Phe Leu Tyr Asp Thr Asn
        595                 600                 605

Val Gly Ala Gly Leu Pro Val Ile Glu Asn Leu Gln Asn Leu Leu Asn
        610                 615                 620

Ala Gly Asp Glu Leu Met Lys Phe Ser Gly Ile Leu Ser Gly Ser Leu
625                 630                 635                 640

Ser Tyr Ile Phe Gly Lys Leu Asp Glu Gly Met Ser Phe Ser Glu Ala
                645                 650                 655

Thr Thr Leu Ala Arg Glu Met Gly Tyr Thr Glu Pro Asp Pro Arg Asp
                660                 665                 670

Asp Leu Ser Gly Met Asp Val Ala Arg Lys Leu Leu Ile Leu Ala Arg
        675                 680                 685

Glu Thr Gly Arg Glu Leu Glu Leu Ala Asp Ile Glu Ile Glu Pro Val
        690                 695                 700

Leu Pro Ala Glu Phe Asn Ala Glu Gly Asp Val Ala Ala Phe Met Ala
705                 710                 715                 720

Asn Leu Ser Gln Leu Asp Asp Leu Phe Ala Ala Arg Val Ala Lys Ala
                725                 730                 735

Arg Asp Glu Gly Lys Val Leu Arg Tyr Val Gly Asn Ile Asp Glu Asp
                740                 745                 750

Gly Val Cys Arg Val Lys Ile Ala Glu Val Asp Gly Asn Asp Pro Leu
        755                 760                 765
```

```
Phe Lys Val Lys Asn Gly Glu Asn Ala Leu Ala Phe Tyr Ser His Tyr
        770             775             780

Tyr Gln Pro Leu Pro Leu Val Leu Arg Gly Tyr Gly Ala Gly Asn Asp
785             790             795             800

Val Thr Ala Ala Gly Val Phe Ala Asp Leu Leu Arg Thr Leu Ser Trp
                805             810             815

Lys Leu Gly Val
            820

<210> SEQ ID NO 5
<211> LENGTH: 20
<212> TYPE: DNA
<213> ORGANISM: Escherichia coli
<220> FEATURE:
<221> NAME/KEY: misc_feature
<223> OTHER INFORMATION: Primer ThrA1

<400> SEQUENCE: 5
accattacca ccaccatcac                                              20

<210> SEQ ID NO 6
<211> LENGTH: 20
<212> TYPE: DNA
<213> ORGANISM: Escherichia coli
<220> FEATURE:
<221> NAME/KEY: misc_feature
<223> OTHER INFORMATION: Primer ThrA2

<400> SEQUENCE: 6
gctcatattg gcactggaag                                              20
```